United States Patent [19]

Menicucci

[11] Patent Number: 4,522,783

[45] Date of Patent: Jun. 11, 1985

[54] METALLIC ALLOYS TO BE USED IN DENTISTRY

[76] Inventor: Gian F. Menicucci, Via Maggi, 110, Leghorn, Italy

[21] Appl. No.: 493,751

[22] Filed: May 11, 1983

[30] Foreign Application Priority Data

May 14, 1982 [IT] Italy ................ 48429 A/82

[51] Int. Cl.³ .............. C22C 5/02; C22C 5/08
[52] U.S. Cl. .................. 420/503; 420/508; 420/509; 420/510; 420/511; 420/587; 420/590
[58] Field of Search .......... 420/503, 511, 587, 508, 420/510, 509, 590

[56] References Cited

U.S. PATENT DOCUMENTS

| | | | |
|---|---|---|---|
| 1,987,452 | 1/1935 | Taylor | 420/509 |
| 2,050,077 | 8/1936 | Wise | 420/503 |
| 2,304,416 | 12/1942 | Leuser | 420/509 |
| 3,340,050 | 9/1967 | Nielsen et al. | 420/509 |
| 4,007,040 | 2/1977 | Kropp | 420/509 |
| 4,093,453 | 6/1978 | Makino et al. | 420/590 |
| 4,255,191 | 3/1981 | Kropp | 420/503 |

FOREIGN PATENT DOCUMENTS

| | | | |
|---|---|---|---|
| 57149 | 8/1982 | France | 420/503 |
| 361893 | 11/1931 | United Kingdom | 420/510 |
| 1032272 | 6/1966 | United Kingdom | 420/503 |

*Primary Examiner*—L. Dewayne Rutledge
*Assistant Examiner*—Christopher W. Brody
*Attorney, Agent, or Firm*—Laff, Whitesel, Conte & Saret

[57] ABSTRACT

The present invention relates to a method for obtaining metallic alloys, to be used particularly in the field of dentistry.

This method allows to accomplish a basic face-centered cubic lattice adapted to form the alloys, in which a homogeneous distribution of the atoms of the different elements is obtained, by precisely determining the number of atoms of each element forming the alloy, in close numerical relationship with the number of atoms of the other elements; it also allows the achievement of a plurality of alloys consisting of at least three among the following elements: gold, platinum, palladium, silver and copper, these alloys respecting the physico-chemical specifications necessary in the particular field of dentistry.

15 Claims, No Drawings

1

METALLIC ALLOYS TO BE USED IN DENTISTRY

FIELD AND BACKGROUND OF THE INVENTION

The present invention relates to a method for obtaining metallic alloys composed of a combination of several metallic elements, to be used in dentistry.

A great number of alloys for dental applications are in commun use; they are composed of different combinations of the most used elements for such applications, such as gold, platinum, palladium, silver and copper with the addition of a certain number of other elements introduced therein in order to comply with specific requirements or to fulfil peculiar functions.

The alloys normally used, owing to the lack of data concerning their properties, are essentially of empirical origin, the studying and producing of the same being almost exclusively based on the fundamental principles and essential features of its composing elements and on the experimental results of tests.

The formulating of a satisfactory general theory concerning the metallic alloys has not yet reached its achievement and still requires much work based on the experimental and theoretical data in order to define and understand the numerous factors influencing the structure of the alloy-forming phases and the complexity of the interactions which the different elements exert on each other.

The main factors concerning the solid-state solubility between several elements can be summarized as follows:

size of atoms; a favourable condition is that of a maximum difference in sizes of 15%;

type of crystal lattice; only the elements having the same crystal lattice allow the formation of complete series of substitution solid solutions;

the same valence; metals having the same valence are more suitable to form substitution solid solutions.

Keeping in mind these factors and the fact that if a metal should have a perfectly regular crystal structure, that is to say devoid of simple or multiple vacancies or dislocations, it could exhibit quite superior qualities with respect to those found in reality, it appears necessary, when forming alloys, to achieve the best distribution and uniformity of the elements in the crystal lattice; on the contrary, it is usually possible to notice an almost causal distribution of the solute atoms in the solvent lattice and, as a result, the presence of vacancies and dislocations.

The atoms of the elements in use respect the above mentioned characteristics required for the formation of substitution solid solutions, as well as the physico-chemical properties suitable for dental applications but the alloys actually in use, owing to their empirical formulas, do only casually possess all the necessary mechanical and electro-chemical features which can only be obtained by forming a perfectly uniform and balanced lattice.

OBJECTS

It is therefore an object of the present invention to achieve a homogeneous and uniform distribution of the atoms of the elements constituting the alloy at the inside of the crystal lattice, ensuring an improved electro-chemical homogeneity in order to achieve the highest resistance to the action of oxidizing and sulfurating chemical agents and simultaneously a greater phisico-chemical resistance of the alloy crystal structure. Furthermore, such homogeneous and uniform distribution must be accomplished while respecting the physico-chemical specifications (ductility, malleability, corrosion strength, etc.) dictated by the particular dental applications and using the lowest indispensable quantity of copper, this element controlling the alloy melting range, but causing the formation of electrochemical cells with the other nobler elements and being easy to oxidize and sulphurize. Finally, from the above purposes it results a plurality of alloys consisting of different combinations of the above mentioned elements exhibiting a homogeneous crystal lattice and physico-chemical characteristics suitable for the specifications concerning these particular applications.

SUMMARY OF THE INVENTION

These and other objects are accomplished by a method for obtaining metallic alloys to be used in dentistry and by determining a group of alloys obtained by said method which is generally characterized in that it provides the use of at least three among the following elements: gold Au, platinum Pt, palladium Pd, silver Ag and copper Cu, in percent ratios determined by the single atomic weights thereof, for every element forming the alloy defining a number of atoms in close numerical relationship with the atoms of the other elements, in order to reach a total number of fourteen atoms or a multiple thereof for every alloy, corresponding to the number of atoms constituting a crystal face-centered cubic lattice which exhibits a proper distribution of the atoms of every element; said percent ratios defining an alloy melting point not higher than 1030°–1040° C. for the alloys used just as they are or as a base for synthetic resin coatings, and not lower than 1140°–1150° C. for the alloys used as a base for ceramic coatings, an alloy melting rate not greater than 90° C. and a Vickers hardness in the range from 120 to 1270.

The method of the present invention for obtaining alloys characterized by a homogeneous distribution of atoms in the crystal lattice is based on the fact that for determined concentrations of the elements the solute atoms are distributed uniformly in the lattice. All the elements used, gold Au, platinum Pt, palladium Pd, silver Ag and copper Cu individually exhibit a crystal face-centered cubic lattice and differ from each other, as to the atom sizes, for a maximum of 10,7% and therefore they are in harmony with the factors conditioning the substitution solid solutions.

The crystal lattice of the alloy which is a face-centered cubic lattice too, is achieved by suitably arranging fourteen atoms; in order to obtain a uniform and homogeneous arrangement between the different elements, it is necessary to carry out the formula calculations, so that the percentages of the different elements, deduced by their individual atomic weight, are suitable to ensure a total number of atoms in the solid solution which reflects the ratio existing therebetween in the crystal face-centered cubic lattice as a structural base unit. Obviously, the number of atoms present in the weight unit of the alloy can decrease or increase of more than 30% depending upon the presence therein of elements having a lower specific gravity, such as palladium, silver or copper, or a higher specific gravity, such as gold or platinum, consequently varying the number of the structural base units, that is the number of the face-centered cubes consisting each one of fourteen atoms; it is therefore necessary to calculate the percentages of the single elements in order to maintain the numerical relationship between the different types of atoms as close as possible.

For the purpose the calculation of said percentages by weight based on weight units in the scale of the kilogram, by means of an electronic balance adapted to give millesimal values, appears particularly suitable, being necessary to carry out a rounding off to the nearest upper value in the case of noble metals and to the nearest lower value in the case of copper, which is a critical element owing to its facility to oxidize and sulphurize but which is necessary for adjusting the alloy melting range.

Among all possible formulas it is necessary to choose those having physico-chemical and mechanical features which exclusively concern the dental field and which can be circumscribed keeping in check the following factors:

a melting point not higher than 1030°–1040° C. for the alloys used just as they are or as a base for synthetic resin coatings in order to prevent silver from attracting oxygen during the melting, which can give rise to the formation of microporosities during the solidification phase;

a melting point not lower than 1140°–1150° C. for the alloys used as a base for ceramic coatings;

a melting rate not greater than 90° C. in order to avoid the zonation, that is the uneven new distribution of the atoms of the different elements in the crystal lattice during solidification; in fact if the atoms do not return to a rest state in a short lapse of temperature and therefore in a short lapse of time, the atoms of the same element are inclined to join together and aggregate;

a Vickers hardness varying from a minimum of 120 for annealed alloys to a maximum of 270;

the lowest indispensable amount of copper in order to keep the melting range within predetermined limits said amount corresponding to the maximum quantity allowed by the percentage of noble metals present therein in order to avoid any risk of oxidation and sulphurization.

Referring to the above mentioned characteristics and to the physico-chemical limits concerning the possibility of utilizing an alloy in the dental field, the formation of a plurality of alloys consisting of different combinations of at least three among the above mentioned elements is achieved. The different types of alloys are listed hereinafter; they are formulated in accordance with the present invention, grouped according to conventional names, the amounts of the single elements being pointed out according to percentages by weight, global titre of noble metals expressed in g/1000 and specific gravity of the alloy.

DESCRIPTION OF THE PREFERRED EMBODIMENTS

| PALLADIUM SILVER ALLOYS | | |
|---|---|---|
| Au | — | — |
| Pt | — | — |
| Pd | 7.266 | 14.546 |
| Ag | 88.395 | 81.110 |
| Cu | 4.339 | 4.344 |
| TITRE °/oo (Pd) | 72.66 | 145.46 |
| SPECIFIC GRAVITY | 10.53 | 10.64 |

These ternary alloys provide a crystal face-centered cubic lattice having no more than an atom of copper, in order to avoid the risks of oxidation and/or sulphurization of this element as much as possible, in percentages varying from a minimum of g 4.339% to a maximum of g 4.344%, according to the presence of one or two atoms of palladium respectively in corresponding percentages of g 7.266% and g 14.546%, with a melting range not higher than 60° C. Silver is present with 11 or 12 atoms for every lattice in percentages of g 81.110% and g 88.395% respectively.

| WHITE GOLD ALLOYS | | | | |
|---|---|---|---|---|
| Au | 12.680 | 12.692 | 23.983 | 24.005 |
| Pt | — | — | — | — |
| Pd | 6.489 | 13.711 | 6.478 | 12.967 |
| Ag | 76.381 | 69.503 | 65.671 | 59.157 |
| Cu | 4.090 | 4.094 | 3.868 | 3.871 |
| TITRE °/oo (Au + Pd) | 195.29 | 264.03 | 304.61 | 369.72 |
| SPECIFIC GRAVITY | 11.64 | 11.75 | 12.64 | 12.74 |

For these quaternary alloys formulas have been chosen providing no more than an atom of copper in the crystal face-centered cubic lattice in percentages varying from a minimum of g 3.868% to a maximum of g 4.094% according to the content of the other elements present in said formulas. Palladium is present with a minimum of 1 atom and a maximum of 2 atoms for each crystal lattice in percentages varying from a minimum of g 6.478% to a maximum of g 13.711% in order to avoid too high melting points and above all to have melting ranges not greater than 90° C. Among these formulas having a high silver content the preference has been given to those having a melting point which does not remarkably exceed the silver melting point in order to avoid silver from attracting oxygen which is then liberated during the alloy solidification process, which gives rise to a particular microporosity called "pinhole microporosity". Silver is present with a number of atoms varying from a minimum of 9 to a maximum of 11, in minimum and maximum percentages of g 59.157% and g 76.381% respectively. In these alloys gold is present with one to two atoms for each crystal lattice in percentages varying from a minimum of g 12.680% to a maximum of g 24.005%.

| YELLOW PALLADIUM GOLD ALLOYS | | | | | |
|---|---|---|---|---|---|
| Au | 34.124 | 43.272 | 51.566 | 52.792 | 59.121 |
| Pt | — | — | — | — | — |
| Pd | 6.145 | 5.844 | 5.571 | 5.703 | 5.323 |
| Ag | 56.062 | 47.395 | 39.536 | 34.693 | 32.378 |
| Cu | 3.699 | 3.489 | 3.327 | 6.812 | 3.178 |
| TITRE °/oo (Au + Pd) | 402.69 | 491.16 | 571.37 | 584.95 | 644.44 |
| SPECIFIC GRAVITY | 13.53 | 14.33 | 15.06 | 15.12 | 15.73 |
| Au | 60.463 | 67.464 | 68.960 | 73.880 | 75.449 |
| Pt | — | — | — | — | — |
| Pd | 5.443 | 5.206 | 5.322 | 4.989 | 5.095 |
| Ag | 27.593 | 21.112 | 16.185 | 15.173 | 10.329 |
| Cu | 6.501 | 6.218 | 9.533 | 5.958 | 9.127 |
| TITRE °/oo (Au + Pd) | 659.06 | 726.70 | 742.82 | 788.69 | 805.44 |

| YELLOW PALLADIUM GOLD ALLOYS | | | | | |
|---|---|---|---|---|---|
| SPECIFIC GRAVITY | 15.80 | 16.41 | 16.49 | 16.98 | 17.07 |

In these alloys gold varies from a minimum of 3 to a maximum of 8 atoms for every crystal lattice and has corresponding minimum and maximum percentages of g 34.124% and g 75.449%. Palladium is present in the quantity of 1 atom for each crystal lattice in percentages varying according to the other composing elements from a minimum of g 4.989% to a maximum of g 6.145%. The quantities shown for palladium, while ensuring a sufficient hardness to allow the alloy to be used in dentistry, avoid a high melting point which never exceeds 1015° C. and therefore the risk that silver may attract oxygen above all in case of alloys having the highest silver content, ensuring at the same time a melting range not greater than 85° C. in order to prevent the zonation phenomenon too and consequently the uneven distribution of the atoms of the different elements at the inside of the crystal lattice. Copper is present in quantities varying from a minimum of 1 atom to a maximum of 3 atoms for each crystal lattice, in corresponding percentages varying from a minimum of g 3.178% to a maximum of g 9.533% in the alloys having a higher gold and palladium content, this element being necessary in order to reduce the melting range in the alloys having a higher content of noble metals, since the risks of oxidation and/or sulphurization of the same decrease when gold and palladium contents increase. Finally, silver is present in quantities varying from a minimum of 2 to a maximum of 9 atoms in corresponding percentages of g 10.329% to g 56.062%.

| YELLOW PLATINUM GOLD ALLOYS | | | | | |
|---|---|---|---|---|---|
| Au | 57.120 | 55.160 | 58.414 | 56.412 | 54.407 |
| Pt | 1.951 | 3.903 | 1.995 | 3.990 | 5.987 |
| Pd | tc — | — | — | — | — |
| Ag | 37.753 | 37.760 | 33.093 | 33.099 | 33.106 |
| Cu | 3.176 | 3.177 | 6.498 | 6.499 | 6.500 |
| TITRE °/oo (Au + Pt) | 590.71 | 590.63 | 604.09 | 604.02 | 603.94 |
| SPECIFIC GRAVITY | 15.68 | 15.72 | 15.75 | 15.79 | 15.83 |
| Au | 65.023 | 62.629 | 66.464 | 64.017 | 71.538 |
| Pt | 2.386 | 4.772 | 2.438 | 4.877 | 2.285 |
| Pd | — | — | — | — | — |
| Ag | 26.377 | 26.383 | 21.570 | 21.575 | 20.222 |
| Cu | 6.214 | 6.212 | 9.528 | 9.531 | 5.955 |
| TITRE °/oo (Au + Pt) | 674.09 | 674.01 | 689.02 | 688.94 | 738.23 |
| SPECIFIC GRAVITY | 16.38 | 16.43 | 16.47 | 16.51 | 16.95 |
| Au | 70.774 | 73.056 | 72.276 | 70.715 | 69.154 |
| Pt | 3.048 | 2.334 | 3.113 | 4.670 | 6.227 |
| Pd | — | — | — | — | — |
| Ag | 20.222 | 15.487 | 15.488 | 15.490 | 15.493 |
| Cu | 5.955 | 9.123 | 9.123 | 9.125 | 9.126 |
| TITRE °/oo (Au + Pt) | 738.22 | 753.90 | 753.89 | 753.85 | 753.81 |
| SPECIFIC GRAVITY | 16.96 | 17.04 | 17.05 | 17.09 | 17.12 |
| Au | 77.532 | 76.798 | 79.109 | 78.362 | 76.866 |
| Pt | 2.194 | 2.927 | 2.239 | 2.985 | 4.478 |
| Pd | — | — | — | — | — |
| Ag | 14.558 | 14.558 | 9.903 | 9.903 | 9.905 |
| Cu | 5.716 | 5.717 | 8.749 | 8.750 | 8.751 |
| TITRE °/oo (Au + Pt) | 797.26 | 797.25 | 813.48 | 813.47 | 813.44 |
| SPECIFIC GRAVITY | 17.47 | 17.49 | 17.57 | 17.58 | 17.61 |
| Au | 75.370 | | | | |
| Pt | 5.972 | | | | |
| Pd | — | | | | |
| Ag | 9.906 | | | | |
| Cu | 8.752 | | | | |
| TITRE °/oo (Au + Pt) | 813.42 | | | | |
| SPECIFIC GRAVITY | 17.65 | | | | |

In these alloys the number of gold atoms varies from a minimum of 6 to a maximum of 9 for each crystal lattice, for corresponding minimum and maximum percentages of g 57.120% and g 79.109%. Platinum, at its lowest percentage of g 1.951%, replaces one atom of gold every five crystal lattices, while at its highest percentage of g 6.227% replaces one atom of gold every three crystal lattices. Beyond this percentage which is considered as the highest advisable one, based on the experimental data, the melting point is extremely high and, as a result, there is the risk that silver may attract oxygen; furthermore, the melting range is greater than 90° C., the highest recommended degree, and there is the risk of zonation. The lowest platinum percentages are provided when for some dental uses high-hardness alloys are not required. Copper is present with a minimum of 1 and a maximum of 3 atoms for every crystal lattice in minimum and maximum percentages of g 3.176% and g 9.531% respectively in the alloys having a higher gold and platinum content, this amount being however sufficient to reduce the melting ranges within such limits that the risk of zonation can be avoided during the solidification process, while at the same time it is ensured a reasonable melting point even when the alloys have the highest gold and platinum content. In these alloys silver is present with a minimum of 2 and a maximum of 7 atoms for every crystal lattice for corresponding percentages varying from g 9.903% to g 37.760%.

| YELLOW PLATINUM AND PALLADIUM GOLD ALLOYS | | | | | |
|---|---|---|---|---|---|
| Au | 42.854 | 43.913 | 42.750 | 43.805 | 42.580 |
| Pt | 2.123 | 2.175 | 2.647 | 2.712 | 3.515 |
| Pd | 4.630 | 4.745 | 4.330 | 4.436 | 3.833 |
| Ag | 46.937 | 42.085 | 46.825 | 41.982 | 46.638 |
| Cu | 3.456 | 7.082 | 3.448 | 7.065 | 3.434 |
| TITRE °/oo (Au + Pt + Pd) | 496.07 | 508.33 | 497.27 | 509.53 | 499.28 |
| SPECIFIC GRAVITY | 14.51 | 14.54 | 14.55 | 14.60 | 14.63 |
| Au | 43.627 | 52.295 | 51.968 | 59.918 | 61.296 |
| Pt | 3.600 | 2.072 | 3.431 | 1.978 | 2.023 |
| Pd | 3.927 | 4.520 | 3.743 | 4.316 | 4.415 |
| Ag | 41.810 | 34.366 | 34.152 | 27.345 | 22.380 |
| Cu | 7.036 | 6.747 | 6.706 | 6.443 | 9.886 |
| TITRE °/oo (Au + Pt + Pd) | 511.54 | 588.87 | 591.42 | 662.12 | 677.34 |
| SPECIFIC GRAVITY | 14.68 | 15.28 | 15.38 | 15.95 | 16.02 |
| Au | 59.562 | 62.738 | 60.923 | 62.348 | 66.740 |
| Pt | 3.277 | 2.072 | 3.352 | 3.430 | 2.361 |
| Pd | 3.575 | 4.519 | 3.657 | 3.742 | 3.863 |
| Ag | 27.182 | 17.179 | 22.242 | 17.072 | 20.885 |
| Cu | 6.404 | 13.492 | 9.826 | 13.408 | 6.151 |
| TITRE °/oo (Au + Pt + Pd) | 664.14 | 693.29 | 679.32 | 695.20 | 729.64 |
| SPECIFIC GRAVITY | 16.05 | 16.10 | 16.13 | 16.20 | 16.59 |
| Au | 66.503 | 68.203 | 67.955 | 69.733 | 69.473 |
| Pt | 3.136 | 2.412 | 3.205 | 2.466 | 3.277 |
| Pd | 3.421 | 3.948 | 3.496 | 4.036 | 3.574 |
| Ag | 20.811 | 16.008 | 15.949 | 10.911 | 10.870 |
| Cu | 6.129 | 9.429 | 9.395 | 12.854 | 12.806 |

-continued

| YELLOW PLATINUM AND PALLADIUM GOLD ALLOYS | | | | | |
|---|---|---|---|---|---|
| TITRE °/oo (Au + Pt + Pd) | 730.70 | 745.63 | 746.56 | 762.35 | 763.24 |
| SPECIFIC GRAVITY | 16.65 | 16.67 | 16.73 | 16.76 | 16.82 |
| Au | 74.656 | 74.395 | 76.258 | 75.986 | |
| Pt | 2.310 | 3.070 | 2.360 | 3.136 | |
| Pd | 3.782 | 3.350 | 3.862 | 3.420 | |
| Ag | 10.221 | 10.185 | 5.220 | 5.202 | |
| Cu | 9.031 | 9.000 | 12.300 | 12.256 | |
| TITRE °/oo (Au + Pt + Pd) | 807.48 | 808.15 | 824.80 | 825.42 | |
| SPECIFIC | 17.24 | 17.29 | 17.33 | 17.39 | |

The choice of these alloys results from the requirement of formulas giving a certain hardness without reaching very high melting points and too wide melting ranges. Therefore palladium partially replaces platinum for the above purposes and platinum and palladium together vary from a minimum of g 6.092% to a maximum of g 7.527%; so, in this range, adding suitable percentages of copper it is possible to achieve melting ranges not wider than 95° C. and melting points not higher than 1040° C. Gold varies from a minimum of 5 to a maximum of 8 atoms in corresponding percentages of g 42.580% and g 76.258%. Platinum varies from a minimum of g 2.023% to a maximum of g 3.600%, while palladium varies from a minimum of g 3.350% to a maximum of g 4.745% and together in their corresponding percentages suggested by the different formulas replace an atom of gold for every lattice. Copper varies from a minimum of 1 atom to a maximum of 4 atoms for every crystal lattice in corresponding percentages varying from a minimum of g 3.434% to a maximum of g 13.408% in the alloys having a higher content of noble metals. Finally, silver is present in quantities in the range from 1 to 8 atoms in percentages varying respectively from g 5.202% to g 46.937%.

| BASIC WHITE AND YELLOW GOLD ALLOYS FOR CERAMIC (WITHOUT COPPER) | | | | | |
|---|---|---|---|---|---|
| Au | 31.714 | 31.739 | 40.356 | 40.386 | 48.243 |
| Pt | 10.472 | 10.479 | 9.993 | 10.000 | 9.557 |
| Pd | 5.710 | 11.430 | 5.450 | 10.908 | 5.212 |
| Ag | 52.104 | 46.352 | 44.201 | 38.706 | 36.988 |
| TITRE °/oo (Au + Pt + Pd) | 478.96 | 536.48 | 557.99 | 612.94 | 630.12 |
| SPECIFIC GRAVITY | 14.51 | 14.61 | 15.23 | 15.31 | 15.86 |
| Au | 55.470 | 62.118 | 68.252 | 73.930 | 79.202 |
| Pt | 9.157 | 8.789 | 8.450 | 8.136 | 7.845 |
| Pd | 4.995 | 4.794 | 4.608 | 4.438 | 4.278 |
| Ag | 30.378 | 24.299 | 18.690 | 13.496 | 8.675 |
| TITRE °/oo (Au + Pt + Pd) | 696.22 | 757.01 | 813.10 | 865.04 | 913.25 |
| SPECIFIC GRAVITY | 16.45 | 16.99 | 17.50 | 17.96 | 18.39 |
| Au | 71.335 | 76.518 | | | |
| Pt | 15.701 | 15.158 | | | |
| Pd | 4.282 | 4.134 | | | |
| Ag | 8.682 | 4.190 | | | |
| TITRE °/oo | 913.18 | 958.10 | (Au + Pt + Pd) | | |
| SPECIFIC GRAVITY | 18.55 | 18.95 | | | |

Gold, in these alloys, is present in quantities varying from a minimum of 3 to a maximum of 10 atoms with corresponding percentages in the range from minimum of g 31.714% in white alloys to a maximum of g 79.202% in yellow alloys. Platinum is present in quantities varying from 1 to 2 atoms for each crystal lattice in corresponding percentages of g 7.848% and g 15.701%. Palladium is present with 1 or 2 atoms in percentages of g 4.134% in yellow alloys up to a maximum of g 11.430% in white alloys. Silver is present in quantities varying from 1 to 9 atoms for every crystal lattice in percentages varying from a minimum of g 4.190% in yellow alloys to a maximum of g 52.104% in white alloys. In every alloy of this kind there is also an iron and platinum compound according to the formula $FePt_3$ in quantities of g 1.116% of iron and g 11.704% of platinum, these quantities being intended for every 1000 grams of basic alloy considered as gold, platinum, palladium and silver; this addition gives the alloy a particular hardness, as the iron, taking up platinum, allows the adding of further platinum in order to ensure a sufficient presence of atoms for an even distribution in the crystal lattice.

In the above mentioned alloys it is also provided the addition of very small quantities of other elements such as indium, ruthenium, iridium or rhodium in maximum amounts in the range of g 0.03% which act as catalysts for crystal aggregation in order to have a fine-grained crystallization of the alloys.

Obviously, any of the specific gravities referred to in the above mentioned formulas can be reproduced by means of other empirical combinations and the global titre of noble metals as well can be achieved by means of a series of different empirical combinations; however when a determined specific gravity of a formula has been given, as well as the corresponding global titre of noble metals, the remaining metal percentages can but be that of the formula itself; in other words, when a determined specific gravity of a formula has been given as well as the millesimal composition of any one of the components thereof, the other components can but be present in the millesimal percentages designed by the formula itself.

The selected formulas, based on the reference principles and parameters mentioned above, according to the method of the present invention, allow the achievement of a homogeneous, uniform and constant composition of the crystal lattice of the different types of alloys, give a more homogeneous electro-chemical point-to-point bond and therefore offer a greater resistance to the action of the oxidizing and sulfurating chemical agents which are present in the oral cavity, as well as a greater physico-mechanical resistance.

What is claimed is:

1. A metallic dental alloy containing at least one crystal face-centered cubic lattice wherein each lattice contains 14 atoms of metal and herein each lattice has 1 atom of copper, 1 or 2 atoms of palladium, 9, 10 or 11 atoms of silver and 1 or 2 atoms of gold.

2. A metallic dental alloy containing at least one crystal face-centered cubic lattice wherein each lattice contains 14 atoms of metal and wherein each lattice has 3, 4, 5, 6, 7 or 8 atoms of gold, 1 atom of palladium, 1, 2, or 3 atoms of copper and 2, 3, 4, 5, 6, 7, 8 or 9 atoms of silver.

3. A metallic dental alloy containing at least one crystal face-centered cubic lattice wherein each lattice contains 14 atoms of metal and wherein each lattice has 6, 7, 8 or 9 atoms of gold, 1, 2 or 3 atoms of copper, 2, 3, 4, 5, 6 or 7 atoms of silver and platinum is present in a sufficient quantity for replacing 1 atom of gold every 3 to 5 crystal lattices.

4. The alloy of claim 1 which is selected from a group of alloys consisting of:

(1) 12.680% of Au, 6.849% Pd, 76.381% Ag and 4.090% Cu;
(2) 12.692% of Au, 13.711% Pd, 69.503% Ag and 4.094% Cu;
(3) 23.983% of Au, 6.478% Pdd, 65.671% Ag and 3.868% Cu; and
(4) 24.005% of Au, 12.967% Pd, 59.157% Ag and 3.871% Cu.

5. The alloy of claim 2 which is selected from a group of alloys consisting of:
(1) 34.124% of Au, 6.145% Pd, 56.062% Ag and 3.669% Cu;
(2) 43.272% of Au, 5.844% Pd, 47.395% Ag and 3.489% Cu;
(3) 51.566% of Au, 5.571% Pd, 39.536% Ag and 3.327% Cu;
(4) 52.792% of Au, 5.703% Pd, 34.693% Ag and 6.812% Cu;
(5) 59.121% of Au, 5.323% Pd, 32.378% Ag and 3.178% Cu;
(6) 60.463% of Au, 5.443% Pd, 27.593% Ag and 6.501% Cu;
(7) 67.464% of Au, 5.206% Pd, 21.112% Ag and 6.218% Cu;
(8) 68.960% of Au, 5.322% Pd, 16.185% Ag and 9.533% Cu;
(9) 73.880% of Au, 4.989% Pd, 15.173% Ag and 5.958% Cu; and
(10) 75.449% of Au, 5.095% Pd, 10.329% Ag and 9.127% Cu.

6. The alloy of claim 3 which is selected from a group of alloys consisting of:
(1) 57.120% of Au, 1.951% Pt, 37.753% Ag and 3.176% Cu;
(2) 55.160% of Au, 3.903% Pt, 37.760% Ag and 3.177% Cu;
(3) 58.414% of Au, 1.995% Pt, 33.093% Ag and 6.498% Cu;
(4) 56.412% of Au, 3.990% Pt, 33.099% Ag and 6.499% Cu;
(5) 54.407% of Au, 5.987% Pt, 33.106% Ag and 6.500% Cu;
(6) 65.023% of Au, 2.386% Pt, 26.377% Ag and 6.214% Cu;
(7) 62.629% of Au, 4.772% Pt, 26.383% Ag and 6.212% Cu;
(8) 66.464% of Au, 2.438% Pt, 21.570% Ag and 9.528% Cu;
(9) 64.017% of Au, 4.877% Pt, 21.575% Ag and 9.531% Cu;
(10) 71.538% of Au, 2.285% Pt, 20.222% Ag and 5.955% Cu;
(11) 70.774% of Au, 3.048% Pt, 20.222% Ag and 5.955% Cu;
(12) 73.056% of Au, 2.334% Pt, 15.487% Ag and 9.123% Cu;
(13) 72.276% of Au, 3.113% Pt, 14.488% Ag and 9.123% Cu;
(14) 70.715% of Au, 4.670% Pt, 15.490% Ag and 9.125% Cu;
(15) 69.154% of Au, 6.227% Pt, 15.493% Ag and 9.126% Cu;
(16) 77.531% of Au, 2.194% Pt, 14.558% Ag and 5.717% Cu;
(17) 76.798% of Au, 2.927% Pt, 14.558% Ag and 5.717% Cu;
(18) 79.109% of Au, 2.239% Pt, 9.903% Ag and 8.749% Cu;
(19) 78.362% of Au, 2.985% Pt, 9.903% Ag and 8.750% Cu;
(20) 76.866% of Au, 4.478% Pt, 9.905% Ag and 8.751% Cu; and
(21) 75.370% of Au, 5.972% Pt, 9.906% Ag and 8.752% Cu.

7. A metallic dental alloy containing at least one crystal face-centered cubic lattice wherein each lattice contains 14 atoms of metal and wherein the alloy contains 42.580% to 76.258% Au, 1.978% to 3.600% of Pt, 3.350% to 4.745% Pd, 3.434% to 13.492% Cu and 5.202% to 46.937% Ag.

8. A metallic dental alloy containing at least one crystal face-centered cubic lattice wherein each lattice contains 14 atoms of metal and wherein the alloy contains 31.714% to 79.202% Au, 7.845% to 15.701% Pt, 4.134% to 11.430% Pd and 4.190% to 52.104% Ag.

9. The alloy of claim 7 which is selected from a group of alloys consisting of:
(1) 42.854% of Au, 2.123% Pt, 4.630% Pd, 46.937% Ag and 3.456% Cu;
(2) 43.913% of Au, 2.175% Pt, 4.745% Pd, 42.085% Ag and 7.082% Cu;
(3) 42.750% of Au, 2.647% Pt, 4.330% Pd, 46.825% Ag and 3.448% Cu;
(4) 43.805% of Au, 2.712% Pt, 4.436% Pd, 41.982% Ag and 7.065% Cu;
(5) 42.580% of Au, 3.515% Pt, 3.833% Pd, 46.638% Ag and 3.434% Cu;
(6) 43.627% of Au, 3.600% Pt, 3.927% Pd, 41.810% Ag and 7.036% Cu;
(7) 52.295% of Au, 2.072% Pt, 4.520% Pd, 34.366% Ag and 6.747% Cu;
(8) 51.968% of Au, 3.431% Pt, 3.743% Pd, 34.152% Ag and 6.706% Cu;
(9) 59.918% of Au, 1.978% Pt, 4.316% Pd, 27.345% Ag and 6.443% Cu;
(10) 61.296% of Au, 2.023% Pt, 4.415% Pd, 22.380% Ag and 9.886% Cu;
(11) 59.562% of Au, 3.277% Pt, 3.575% Pd, 27.182% Ag and 6.404% Cu;
(12) 62.738% of Au, 2.072% Pt, 4.519% Pd, 17.179% Ag and 13.492% Cu;
(13) 60.923% of Au, 3.352% Pt, 3.657% Pd, 22.242% Ag and 9.826% Cu;
(14) 62.348% of Au, 3.430% Pt, 3.742% Pd, 17.072% Ag and 13.408% Cu;
(15) 66.740% of Au, 2.361% Pt, 3.863% Pd, 20.885% Ag and 6.151% Cu;
(16) 66.503% of Au, 3.136% Pt, 3.421% Pd, 20.811% Ag and 6.129% Cu;
(17) 68.203% of Au, 2.412% Pt, 3.948% Pd, 16.008% Ag and 9.429% Cu;
(18) 67.955% of Au, 3.205% Pt, 3.496% Pd, 15.949% Ag and 9.395% Cu;
(19) 69.733% of Au, 2.466% Pt, 4.036% Pd, 10.911% Ag and 12.854% Cu;
(20) 69.473% of Au, 3.277% Pt, 3.574% Pd, 10.870% Ag and 12.806% Cu;
(21) 74.656% of Au, 2.310% Pt, 3.782% Pd, 10.221% Ag and 9.031% Cu;
(22) 74.395% of Au, 3.070% Pt, 3.350% Pd, 10.185% Ag and 9.000% Cu;
(23) 76.258% of Au, 2.360% Pt, 3.862% Pd, 5.220% Ag and 12.300% Cu;
(24) 75.986% of Au, 3.136% Pt, 3.420% Pd, 5.202% Ag and 12.256% Cu.

10. The alloy of claim 8 which is selected from a group of alloys consisting of:
(1) 31.714% of Au, 10.472% Pt, 5.710% Pd and 52.104% Ag;
(2) 31.739% of Au, 10.479% Pt, 11.430% Pd and 46.352% Ag;
(3) 40.356% of Au, 9.993% Pt. 5.450% Pd and 44.201% Ag;
(4) 40.386% of Au, 10.000% Pt, 10.908% Pd and 38.706% Ag;
(5) 48.243% of Au, 9.557% Pt, 5.212% Pd and 36.988% Ag;
(6) 55.470% of Au, 9.157% Pt, 4.995% Pd and 30.378% Ag;
(7) 62.118% of Au, 8.789% Pt, 4.794% Pd and 24.299% Ag;
(8) 68.252% of Au, 8.450% Pt, 4.608% Pd and 18.690% Ag;
(9) 73.930% of Au, 8.136% Pt, 4.438% Pd and 13.496% Ag;
(10) 79.202% of Au, 7.845% Pt, 4.278% Pd and 8.675% Ag;
(11) 71.335% of Au, 15.701% Pt, 4.282% Pd and 8.682% Ag; and
(12) 76.518% of Au, 15.158% Pt, 4.134% Pd and 4.190% Ag.

11. The alloy of claim 1, wherein it further contains a catalytic amount of about 0.03% of a compound selected from the group consisting of indium, ruthenium, iridum, rodium and mixtures thereof.

12. The alloy of claim 2, wherein it further contains a catalytic amount of about 0.03% of a compound selected from the group consisting of indium, ruthenium, iridum, rodium and mixtures thereof.

13. The alloy of claim 3, wherein it further contains a catalytic amount of about 0.03% of a compound selected from the group consisting of indium, ruthenium, iridum, rodium and mixtures thereof.

14. The alloy of claim 7, wherein it further contains a catalytic amount of about 0.03% of a compound selected from the group consisting of indium, ruthenium, iridum, rodium and mixtures thereof.

15. The alloy of claim 8, wherein it further contains a catalytic amount of about 0.03% of a compound selected from the group consisting of indium, ruthenium, iridum, rodium and mixtures thereof.

* * * * *